United States Patent [19]

Broger et al.

[11] Patent Number: 4,857,648
[45] Date of Patent: Aug. 15, 1989

[54] ISOQUINOLINE DERIVATIVES

[75] Inventors: Emil A. Broger, Magden; Yvo Crameri, Oberwil, both of Switzerland; Bernd Heiser, Inzlingen, Fed. Rep. of Germany

[73] Assignee: Hoffmann-La Roche Inc., Nutley, N.J.

[21] Appl. No.: 268,441

[22] Filed: Nov. 8, 1988

[30] Foreign Application Priority Data

Nov. 11, 1987 [EP] European Pat. Off. ........ 87810651.7

[51] Int. Cl.$^4$ ............................................. C07D 217/20
[52] U.S. Cl. .................................... 546/147; 546/146
[58] Field of Search ................................ 546/146, 147

[56] References Cited

U.S. PATENT DOCUMENTS 3,634,429  1/1972  Leimgruber et al. ............... 546/147
4,514,569  4/1985  Hendrickson et al. ............. 546/146

FOREIGN PATENT DOCUMENTS 0245960  11/1987  European Pat. Off. .

Primary Examiner—Glennon H. Hollrah
Assistant Examiner—James H. Turnipseed
Attorney, Agent, or Firm—Jon S. Saxe; George M. Gould; Julie M. Prlina

[57] ABSTRACT

The invention is concerned with novel isoquinoline derivatives of the formula

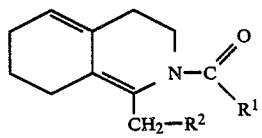

wherein
$R^1$ is hydrogen, lower alkyl, lower alkoxy, aryl, aryloxy, aryl-lower alkyl or aryl-lower alkoxy and
$R^2$ is phenyl or substituted phenyl.

These novel isoquinoline derivatives are valuable intermediates in the manufacture of morphinan derivatives.

5 Claims, No Drawings

ISOQUINOLINE DERIVATIVES

The present invention is concerned with novel isoquinoline derivatives as well as with their manufacture and their use in an asymmetric hydrogenation procedure.

The novel isoquinoline derivatives of the present invention, as well as those obtained therefrom by asymmetric hydrogenation, are valuable intermediates in the synthesis of morphinan derivatives, and particularly of dextromethorphan.

The novel isoquinoline derivatives according to the present invention can be represented by the following formula

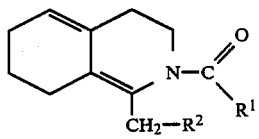

I wherein $R^1$ is hydrogen, lower alkyl, lower alkoxy, aryl, aryloxy, aryl-lower alkyl or aryl-lower alkoxy and $R^2$ is phenyl or substituted phenyl.

In the scope of the present invention the term lower alkyl stands for straight or branched chain alkyl groups with from 1 to 8 carbon atoms, e.g. methyl, ethyl, n-propyl isopropyl, butyl, tert. butyl, pentyl, hexyl, heptyl, octyl and the like. The term aryl means substituted or unsubstituted phenyl or naphthyl groups. The terms lower alkoxy and aryloxy stand for groups in which the alkyl and aryl moieties have the foregoing meanings. The terms aryl-lower alkyl and aryl-lower alkoxy stand for groups in which the aryl moiety has the foregoing meaning and the lower alkyl and lower alkoxy moieties mean groups with 1 to 3 carbon atoms, e.g. benzyl and benzyloxy groups. The term halogen stands for fluorine, chlorine, bromine and iodine; chlorine and bromine being preferred.

In connection with the ligands of formulae VII and VIII, the phenyl and benzyl groups can be not only unsubstituted, but also substituted in the ortho, meta or para position or also multiply substituted. As substituents there come into consideration lower alkyl or lower alkoxy groups, preferably methyl or methoxy groups, di-lower alkylamino groups, preferably dimethylamino groups, and fluorine. The term "lower alkyl" signifies in this connection straight-chain or branched-chain alkyl groups containing 1 to 4 carbon atoms such as methyl, ethyl, propyl, isopropyl, n-butyl, isobutyl and tert. butyl. The terms "lower alkoxy", "di-lower alkylamino" and "lower alkoxycarbonyl" signify groups in which the alkyl moiety has the foregoing significance. The term "lower alkylene" signifies dimethylene or trimethylene. As protecting groups for the hydroxymethyl group there come into consideration in this connection especially the customary ether-forming groups such as, for example, benzyl, methyl, tert. butyl methoxymethyl and the like, and ester-forming groups such as, for example, acetyl, benzoyl and the like.

The notation " " signifies that the corresponding residue is situated above the plane of the molecule and the notation " " signifies that the corresponding residue is situated below the plane of the molecule.

The compounds of formula I in accordance with the invention can be manufactured by a process which is characterized in that (a) an isoquinoline derivative of the formula

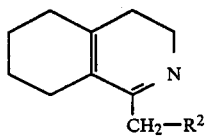

II wherein $R^2$ has the above meanings, is reacted with an acylating agent of the formula

III wherein $R^1$ has the above meanings and X is halogen or a group of the formula

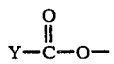

wherein Y is lower alkyl, or in that (b) an isoquinoline derivative of the following formula in the E-form

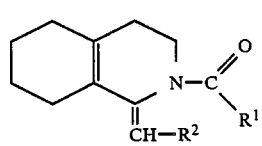

IV wherein $R^1$ and $R^2$ have the above meanings, isomerized.

The acylation of a compound of formula II with an acylating agent of formula III can be carried out in an inert organic solvent in the presence of a base and at a temperature of from about −20° C. to about 50° C., preferably from about 0° C. to about 20° C. As suitable solvents for this reaction there can be used aprotic solvents such as aliphatic or aromatic hydrocarbons, e.g. hexane, benzene, toluene or also halogenated hydrocarbons e.g. methylene chloride, chloroform and the like, or also ethers such as diethyl ether, tetrahydrofuran, dioxan and the like. As bases which can be used in this reaction there can be named amines such as e.g. triethylamine or pyridine, or also alkali and earth alkali metal salts of organic acids, such as e.g. sodium formiate, sodium acetate and the like. Furthermore, this reaction is carried out under inert gas, e.g. under nitrogen, argon and so on.

The isomerization of the E-form of an isoquinoline derivative of formula IV can be carried out by heating in a chlorinated hydrocarbon or in a chlorinated hydrocarbon containing solvent or also catalytically.

The heating in a chlorinated hydrocarbon or in a chlorinated hydrocarbon containing solvent can be carried at temperatures of from about 50° C. to about 200° C., preferably from about reflux temperature to about 150° C., if necessary under pressure. As chlorinated hydrocarbons there can be used those which are usually used as solvents, such as e.g. methylene chloride, chloroform, 1,2-dichloroethane and the like. As the solvent there can be used in this connection a lower alkanol with 1 to 5 carbon atoms, such as e.g. methanol, ethanol, propanol and the like. A preferred chlorinated hydrocarbon containing solvent is methanol containing methylene chloride.

The catalytic isomerization can be carried out in an inert organic solvent at a temperature of from about 0° C. to about 200° C., if necessary under pressure of an inert gas or hydrogen, preferably at a temperature of from about room temperature to about 150° C. As the inert organic solvent there can be used aromatic hydrocarbons, e.g. benzene or toluene, ethers such as tetrahydrofuran or dioxan or also chlorinated hydrocarbons such as methylene chloride, chloroform, 1,2-dichloroethane and the like. Furthermore, there can be used mixtures of chlorinated hydrocarbons and lower alkanols, preferably mixtures of methylene chloride and methanol. As catalysts for this catalytic isomerization there can be used common isomerization catalysts. Examples of such catalysts are e.g. hydrogen halides such as hydrogen chloride or hydrogen bromide, iodine, palladium complexes e.g. palladium acetate, Pd Cl$_2$(CH$_3$CN)$_2$, ruthenium complexes e.g. Ru(Z)$_2$L$_n^1$ wherein Z is halogen or a group A—COO$^-$, A is lower alkyl, aryl, halogenated lower alkyl or halogenated aryl and L$^1$ is a mono- or diphosphine ligand such as e.g. triphenylphosphine, tricyclohexylphosphine or also a ligand of formulae VII or VIII or (6,6'-dimethyl-2,2'-biphenylylene)bis(dicylclohexylphosphine) and the like and n is 1 or 2.

The asymmetric hydrogenation of isoquinoline derivatives of formula I yields compounds of the formula

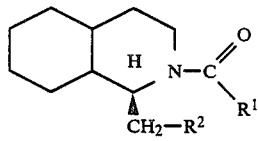

V wherein R$^1$ and R$^2$ have the above meanings.

This asymmetric hydrogenation is carried out, according to the present invention, in the presence of a ruthenium catalyst of the formula Ru(Z)$_2$L$^2$    VI wherein Z is halogen or a group A—COO$^-$, A is lower alkyl, aryl, halogenated lower alkyl or halogenated aryl and L$^2$ is a ligand of the formula

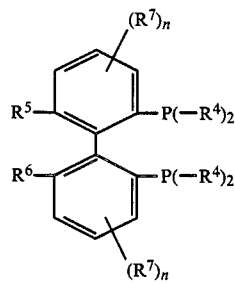

VII wherein R$^4$ signifies phenyl R$^5$ and R$^6$, which can be the same or different, signify hydrogen, lower alkyl, lower alkoxy, di-lower alkylamino or protected hydroxymethyl or R$^5$ and R$^6$ together signify the group $$(-CH_2-)_{m'}, \ -CH_2-O-CH_2-, \ \begin{array}{c}-CH_2\\ \phantom{x} \\ -CH_2\end{array}\!\!\!\!N-R^8 \ \text{or}$$

$$\begin{array}{c}-CH_2\\ \phantom{x} \\ -CH_2\end{array}\!\!\!\!C\!\!\!\!\begin{array}{c}OR^9\\ \phantom{x} \\ OR^9\end{array}$$

in which m represents a number 3 to 5, R$^8$ represents lower alkyl, phenyl or benzyl and R$^9$ represents lower alkyl or both R$^9$ together represent dimethylene or trimethylene, R$^7$ signifies methyl, lower alkoxy, di-lower alkylamino or fluorine and n signifies the number 0, 1, 2 or 3,
or of the formula

VIII wherein R$^4$ has the above meaning and the naphthalene rings are optionally substituted in the ortho-position with methyl, ethyl, halogen, di-lower alkylamino or lower alkoxy.

The term halogenated lower alkyl means lower alkyl groups with a variable number of halogen atoms, particularly chlorine or fluorine, at least one thereof being in alpha position to the —COO$^-$ group. Preferred halogenated lower alkyl groups are perfluorinated lower alkyl groups, e.g. trifluoromethyl, pentafluoroethyl and the like.

Preferred ligands are those of formula VII and, furthermore, those of formula VII in which R$^4$ signifies unsubstituted phenyl or phenyl substituted with methyl, R$^5$ and R$^6$ are the same and signify lower alkyl or R$^5$ and R$^6$ together signify the group —CH$_2$—O—CH$_2$—, n signifies the number 0 or 1 and R$^7$ signifies methyl, fluorine or di-lower alkylamino. Insofar as n signifies the number 1, the substituent R$^7$ is preferably situated in the m-position to the phosphorus.

Examples of most preferred ligands of formula VII are (S)-(6,6'-dimethyl-2,2'-biphenylylene)bis(diphenylphosphine); (S)-(6,6'-dimethyl-2,2'-biphenylylene)bis(di-p-tolylphosphine).

The ligands of formulae VII and VIII are known compounds, e.g. from European Patent No. 104 375 and from Japanese Patent Application No. 136 605/1978.

The ruthenium catalysts of formula VI can be manufactured in a manner known per se. They can be manufactured, for example, by reacting a ruthenium complex of the formula

[Ru(Z$^1$)$_2$L$_m^3$]$_n$·(H$_2$O)$_p$    IX wherein Z$^1$ is halogen or a groups A$^1$—COO$^-$, A$^1$ is halogenated lower alkyl, L$^3$ is a neutral ligand, m is 1, 2 or 3, n is 1 or 2 and p is 0 or 1,
with a chiral disphosphine ligand of formula VII or VIII or by reacting a ruthenium complex of the formula $Ru(CF_3COO)_2L^2$  X wherein $L^2$ has the above meanings,
with a salt containing the anion Z, wherein Z has the above meanings.

The term "neutral ligand" signifies in the scope of the present invention a readily exchangeable ligand such as a diolefin, e.g. norbornadiene, 1,5-cyclooctadiene and the like, or a nitrile such as acetonitrile, benzonitrile and the like. If m is 2 or 3, the ligands can be the same or different.

The ruthenium complexes of formula IX which are used as starting materials are known substances or analogous of known substances, which can be prepared readily in an analogy to the known substances e.g. according to Albers, M. O. et al., J. Organomet. Chem., 272 (1984) C62–C66.

The reaction of a ruthenium complex of formula IX with a chiral diphosphine ligand of formulae VII or VIII can be carried out in a manner known per se. This reaction can conveniently be carried out in an inert organic solvent. Examples of such solvents are ethers such as e.g. tetrahydrofuran or dioxan, ketones such as e.g. acetone, lower alcohols such as methanol, ethanol and the like, halogenated hydrocarbons such as methylene chloride, chloroform and the like, or also mixtures of such solvents. The reactin can be carried out at temperature between about 0° C. and about 100° C., preferably at about 15° C. to about 60° C., but with strict exclusion of oxygen.

The reaction of ruthenium complexes of formula X with a salt containing the anion Z can be carrie out according to methods known per se. The term "a salt containing the anion Z" means e.g. alkali metal salts, ammonium salts or other suitable metal salts. In order to increase the solubility, crown ethers can be added in certain cases.

In order to carry out the aforementioned asymmetric hydrogenation, the complexes of formula VI can be first prepared and then added to a solution of a compound to be hydrogenated. Alternatively, they can also be formed in situ in the presence of a compound to be hydrogenated.

The asymmetric hydrogenation can be carried out in suitable organic solvents which are inert under the reaction conditions. As such solvents there can be named, in particular, lower alcanols such as e.g. methanol or ethanol, or mixtures of such alcohols with halogenated hydrocarbons, e.g. methylene chloride, chloform and the like, or with cyclic ethers such as tetrahydrofuran or dioxan and the like. The ratio between ruthenium and the ligand $L^2$ conveniently lies between about 0.5 and about 2 mol, preferably by about 1 mol of ruthenium per mol of ligand. The ratio between ruthenium, in the complexes of formula VI, and the compounds to be hydrogenated conveniently lies between about 0,001 and about 5 mol%, preferably between about 0,01 and about 1,0 mol%.

The asymmetric hydrogenation with the complexes of formula VI can be carried out conveniently at temperatures of about 50° C. to about 200° C., preferably of about 80° C. to about 160° C. This hydrogenation is conveniently effected under pressure, expecially under a pressure of about 5 to 200 bar, preferably 20 to 100 bar.

The following Examples serve to illustrate the invention and are in no way a limitation thereof.

In these Examples the abbreviations have the following significances:
TLC stands for thin layer chromatography·TLC-system: benzene-ethyl acetate 3:2
GC stands for gas chromatography·25 m capillary column PVMS 54 (Perkin Elmer)
TFA stands for trifluoroacetyl For the determination of the e.e., the products were hydrolyzed in a mixture of ethylene glycol and 40% aqueous potassium hydroxide at 170° C. for 18 hours. The resulting amine was converted with (−)-camphanoyl chloride in pyridine/4-dimethylaminopyridine to a mixture of the diastereomeric amides, which was analyzed by GC.
BIPHEMP=(S)-(6,6'-dimethyl-2,2'-biphenylylene)bis(-diphenylphosphine)
CYBIPHEMP=(6,6'-dimethyl-2,2'-biphenylylene)bis(-dichlorohexylphosphine)

EXAMPLE 1

2-Methoxycarbonyl-1-(p-methoxybenzyl)-2,3,4,6,7,8-hexahydroisoquinoline

To a stirred solution of 1-(p-methoxybenzyl)-3,4,5,6,7,8-hexahydroisoquinoline (29.8 g, 0.117 mol) in toluene (500 ml) at 0°–3° under nitrogen was added dropwise methyl chloroformate (13.3 g, 0.14 mol), then triethylamine (13.0 g, 0.129 mol). After stirring the suspension over night at 8°–10°, it was extracted successively with ice water, 2N hydrochloric acid, ice water, 2N sodium hydroxide, ice water and saturated brine. The organic phase was dried over anhydrous magnesium sulfate and concentrated. GC showed the residue (31.2 g, yellow oil) to contain 55.9% of the desired product. Chromatography and crystallization from methanol afforded 15.0 g or pure 2-methoxycarbonyl-1-(p-methoxybenzyl)-2,3,4,5,6,7,8-hexahydroisoquinoline as white crystals; mp 78.5°–80°.

EXAMPLE 2

2-Acetyl-1-(p-methoxyphenyl)-2,3,4,6,7,8-hexyhydroisoquinoline

A solution of (E)-2-acetyl-1,2,3,4,5,6,7,8-octahydro-1-(p-methoxybenzylidene)isoquinoline (2.1 g) in methylene chloride (120 ml) was refluxed under argon for 2 hours. The solvent was removed by distillation at 30°/20 mbar. The residue, 2.3 g of a colorless oil, contained 61% of the desired product according to GC. Column chromatography and crystallization from isopropyl ether yielded 700 mg of pure (TLC, GC) 2-acetyl-1-(p-methoxybenzyl0)-2,3,3,6,7,8-hexahydroisoquinoline as white crystals; mp 48°–50°.

The (E)-2-acetyl-1,2,3,4,5,6,7,8-octahydro-1-(p-methoxybenzylidene)isoquinoline used as starting material was prepared as follows:

To a stirred solution of 0.80 mol of crude 1-(p-methoxybenzyl)-3,4,5,6,7,8-hexahydroisoquinoline (prepared as described by O. Schnider and J. Hellerbach, Helv. Chim. Acta 33, 1437 (1950) in 2 l of toluene was added at 0°–3° under argon within 20 min. 164 g (1.61 mol) of acetic anhydride, and then within 30 min. 204 g (2.01 mol) of triethylamine. The mixture was stirred over night, allowing the temperature to reach gradually 15°–20°. After cooling to 5° the reaction mixture was extracted successively with ice water, 2N hydrochloric acid, ice water, 2N sodium hydroxide, ice water and saturated brine. The organic phase was dried over sodium sulfate and concentrated to give 205 g of a redbrown oil. Column chromatography and crystallization from methanol afforded 41.3 g pure (TLC, GC) (E)-2-acetyl-1,2,3,4,5,6,7,8-octahydro-1-(p-methoxybenzylidene)isoquinoline; mp 74.5°-76°.

EXAMPLE 3

In a glove box (<1 ppm oxygen), a 500 ml steel autoclave was charged with 2-acetyl-1-(p-methoxybenzyl)-2,3,4,6,7,8-hexahydroisoquinoline (2.43 g, 8.17 mmol) (prepared according to example 2) 40 ml of methanol, 28 ml of methylene chloride and 100 ml of a methanol solution containing 0.082 mmol of Ru(TFA)$_2$(BIPHEMP) as catalyst. The hydrogenation was carried out at 100° and 60 bar for 20 h. The solution was concentrated to give an oil, which was dissolved in 300 ml of diethyl ether. To removed the catalyst the ether solution was passed through a short pad of silica gel. Concentration of the filters afforded 2.4 g of (S)-2-acetyl-1-(p-methoxybenzyl)-1,2,3,4,5,6,7,8-octahydroisoquinoline as a colorless oil; e.e. 94.3%.

EXAMPLE 4

In a glove box, a 500 ml steel autoclave was charged with 2-methoxycarbonyl-1-(p-methoxybenzyl)-2,3,4,6,7,8-hexahydroisoquinoline (2.1 g, 6.68 mmol) (prepared according to example 1) 140 ml of methanol, 28 ml of methylene chloride and 0.067 mmol of Ru(TFA)$_2$(BIPHEMP) as catalyst. The hydrogenation was carried out at 140° and 60 bar. After 3 h the conversion was 99.3%. Work-up as described in example 3 gave 1.98 g of yellow crystals; 93.8% e.g. Crystallization from isopropyl ether gave 0.45 g of pure (TLC, GC) (S)-2-methoxycarbonyl-1-(p-methoxybenzyl)-1,2,3,4,5,6,7,8-octahydroisoquinoline as off-white crystals; mp 67°-68°, 99.3% e.e..

EXAMPLE 5

In a glove box, a 500 ml steel autoclave was charged with (E)-2-acetyl-1-(p-methoxybenzylidene)-1,2,3,4,5,6,7,8-octahydroisoquinoline (2.1 g, 7.06 mmol) (prepared according to example 2) 130 ml of methanol, a solution of (+)-CYBIPHEMP (8.2 mg, 0.0142 mmol) and [Ru(TFA)$_2$(COD)]$_2$—(H$_2$O) (6.3 mg, 0.007 mmol) in 30 ml of methylene chloride and 5 ml of a solution of 0.0035 mmol of Ru(TFA)$_2$(BIPHEMP) in methanol. The hydrogenation was run at 100° and 60 bar for 5 h. Work-up as described in example 3 afforded 2.0 g of (S)-2-acetyl-1-(p-methoxybenzyl)-1,2,3,4,5,6,7,8-octahydroisoquinoline, $[\alpha]_D^{20} = +45.9°$ (c=1, methanol), optical purity 86%: e.e. 88.3%.

EXAMPLE 6

A solution of (E)-2-acetyl-1,2,3,4,5,6,7,8-octahydro-1-(p-methoxybenzylidene)isoquinoline (2.1 g) in methylene chloride (120 ml) was refluxed under argon for 2 h. The reaction mixture was concentrated to a final volume of 30 ml at 25°/20 mbar and transferred into a 500 ml autoclave, followed by 90 ml of methanol and 50 ml of a methanol solution containing 0.035 mmol of Ru(TFA)$_2$(BIPHEMP). Hydrogenation at 100°, 60 bar and work-up as described in example 3 afforded 2.08 of (S)-2-acetyl-1-(p-methoxybenzyl)-1,2,3,4,5,6,7,8-octahydroisoquinoline; $[\alpha]_D^{20} = +51.2°$ (c=1, methanol), optical purity 97.3% e.g., 97.6%.

A 800 mg sample was recrystallized from 3.0 ml of diisopropyl ether to give 420 mg of white crystals; mp 80°-81.5°. $[\alpha]_D^{20} +53.0°$ (c=1, methanol), optical purity 99.3%.

EXAMPLE 7

To a solution of 0.5 g of (E)-2-acetyl-1,2,3,4,5,6,7,8-octahydro-1-(p-methoxybenzylidene)isoquinoline in 100 ml of methylene chloride was added at room temperature a solution of anhydrous hydrogen chloride (prepared from 13.2 mg of acetyl chloride and 5.4 mg of methanol) in 10 ml of methylene chloride. The solution was stirred for 0.5 h. GC analysis: 57.1% of 2-acetyl-1-(p-methoxybenzyl)-2,3,4,6,7,8-hexahydroisoquinoline.

EXAMPLE 8

To a solution of 0.1 g of (E)-2-acetyl-1,2,3,4,5,6,7,8-octahydro-1-(p-methoxybenzylidene)isoquinoline in 5 ml of tetrahydrofuran was added at room temperature a solution of 4.3 mg of dichlorobis(acetonitrile)palladium-(II) in 5 ml of tetrahydrofuran. The yellow solution was stirred for 0.5 h. and worked up as described in example 3. GC analysis: 50% of 2-acetyl-1-(p-methoxybenzyl)-2,3,4,6,7,8-hexahydroisoquinoline.

EXAMPLE 9

To a solution of 0.5 g (E)-2-acetyl-1,2,3,4,5,6,7,8-octahydro-1-(p-methoxybenzylidene)isoquinoline in 100 ml of benzene was added at room temperature a solution of 8.5 mg of iodine in 10 ml of benzene. The solution was stirred at room temperature for 0.5 h. The brown solution was extracted successively with 0.1N sodium thiosulfate, water and brine. GC analysis: 74% 2-acetyl-1-(p-methoxybenzyl)-2,3,4,6,7,8-hexahydroisoquinoline.

EXAMPLE 10

The ruthenium catalysts used in previous examples were prepared as follows:

In a glove box (<1 ppm oxygen), a solution of BIPHEMP (38.5 mg, 0.070 mmol) in 80 ml of methanol was added at room temperature to a solution of [Ru(TFA)$_2$(COD)]$_2$(H$_2$O) (31.1 mg, 0.0350 mmol: Eric Singleton et al. J. Organomet. Chem. 272 (1984) C62-C66) in 20 ml of methanol. The solution was stirred for 4 hours, then an aliquote containing the desired amount of catalyst was added to a solution of the substrate.

In a manner analogous to the above the catalysts were also prepared from a solution of [Ru(TFA)$_2$(COD)]$_2$, which was itself prepared as described by E. Singleton et al., but under strictly anhydrous conditions.

EXAMPLE 11

(+)-(6,6')-Dimethyl-2,2'-biphenylylene)bis(dicyclohexylphosphine, (+)-CYBIPHEMP

To 4.0 g of magnesium turnings in a solution of 30 mg of iodine and 0.3 ml of 1,2-dibromoethane in 25 ml of dry tetrahydrofuran was added dropwise within 1 h at 60° and under argon a solution of 10.8 g of 2,2'-dibromo-6,6'-dimethylbiphenyl in 250 ml of dry toluene. The reaction mixture was stirred at 60° for 2.5 h, cooled at room temperature and treated dropwise with a solution of 21.6 g of dicyclohexylphosphinoyl chloride in 100 ml of toluene. When the addition was complete the reaction mixture was stirred at 60° for 3.5 h and cooled to room temperature. After the slow addition of 20 ml of saturated brine, 180 ml of brine was added in one portion. The two-phase mixture was stirred at 60° for 0.5 h. Excess magnesium was removed by filtration. After addition of 650 ml of toluene the organic phase was separated and extracted twice with 300 ml of water. The aqueous phases were washed with 400 ml of methylene chloride. The organic solutions were combined, dried over sodium sulfate and concentrated to dryness at 50°/20 mbar. The crystalline residue (27.5 g) was recrystallized from a mixture of methylene chloride and ethyl acetate giving 10.8 g of racemic CYBIPHEMP dioxide. Chromatography (silica, methylene chloride/methanol 99:1) and recrystallization from toluene/methanol/ethyl/acetate yielded an analytical sample of rac-CYBIPHEMP dioxide, mp >300°.

A solution of 10.6 g of rac-CYBIPHEMP dioxde and 7.3 g of (L)-dibenzoyltartaric acid in 80 ml of methylene chloride and 120 of ethyl acetate was concentrated under reduced pressure until crystals started to form. After having stirred the suspension at room temperature for 5 h the crystals were filtered and dissolved in 400 ml of methylene chloride. The solution was extracted successively with aqueous potassium carbonate solution (pH 10-11) and water, dried over sodium sulfate, and evaporated to dryness affording 5.1 g of (+)-CYBIPHEMP dioxide as white crystals. An analytical sample was prepared by recrystallization from ethyl acetate: $[\alpha]_D^{20} = +67°$ (c−1, chloroform).

Reduction: A glass-lined autoclave was charged under argon and at 0°–3° with 4.6 g of the dioxide, 15 g of trichlorosilane and 300 ml of toluene. The reaction mixture was agitated at 160° and 30 bar argon for 16 h, cooled to 0°, and transferred under careful exclusion of air to a reaction flask. Under stirring, argon and cooling, 3N aqueous sodium hydroxide was added dropwise until the aqueous phase had pH 14. The toluene layer was extracted twice with degassed water and concentrated under reduced pressure to give 4.8 g of (+)-CYBIPHEMP. An analytical sample was prepared by recrystallization from degassed toluene-ethanol: there were obtained white crystals; mp 179.5°–180.5°, $[\alpha]_D^{20} = +80°$ (c=0.5, chloroform).

We claim:

1. A compound of the formula

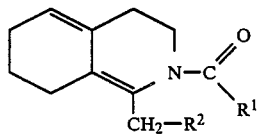

wherein $R^1$ is hydrogen, lower alkyl, lower alkoxy, aryl, aryloxy, aryl-lower alkyl or aryl-lower alkoxy and $R^2$ is phenyl or p-methoxyphenyl.

2. The compound of claim 1, wherein $R^1$ is hydrogen, lower alkyl or lower alkoxy.

3. The compound of claim 2, wherein $R^2$ is p-methoxyphenyl.

4. The compound of claim 3 wherein $R^1$ is lower alkoxy and said compound is 2-methoxycarbonyl-1-(p-methoxybenzyl)-2,3,4,6,7,8-hexahydroisoquinoline.

5. The compound of claim 3 wherein $R^1$ is lower alkyl and said compound is 2-acetyl-1-(p-methoxyphenyl)-2,3,4,5,7,8-hexahydroisoquinoline.

* * * * *